(12) United States Patent
Yamasaki et al.

(10) Patent No.: US 8,043,848 B2
(45) Date of Patent: Oct. 25, 2011

(54) BIOLOGICAL REACTION METHOD AND BIOREACTOR

(75) Inventors: Kazuyuki Yamasaki, Hiroshima (JP); Kazuyuki Sakata, Fukuyama (JP); Kazumi Chuhjoh, Takamatsu (JP); Masaki Kataoka, Fukuyama (JP)

(73) Assignee: Sharp Kabushiki Kaisha, Osaka (JP)

( * ) Notice: Subject to any disclaimer, the term of this patent is extended or adjusted under 35 U.S.C. 154(b) by 1231 days.

(21) Appl. No.: 11/783,671

(22) Filed: Apr. 11, 2007

(65) Prior Publication Data
US 2007/0275452 A1  Nov. 29, 2007

(30) Foreign Application Priority Data
May 26, 2006  (JP) .................................. 2006-146247

(51) Int. Cl.
C12M 1/02 (2006.01)
C12M 1/12 (2006.01)

(52) U.S. Cl. ............... 435/294.1; 435/296.1; 435/297.1; 435/299.1; 435/308.1

(58) Field of Classification Search ............... 435/289.1, 435/294.1, 296.1, 297.2, 299.1, 308.1
See application file for complete search history.

(56) References Cited

U.S. PATENT DOCUMENTS

| 4,156,630 A * | 5/1979 | Muller .......................... 435/261 |
| 4,233,407 A * | 11/1980 | Seebeck et al. ............. 435/296.1 |
| 2006/0191847 A1* | 8/2006 | Yamasaki et al. ............. 210/630 |

FOREIGN PATENT DOCUMENTS

| JP | 2001-178449 | 7/2001 |
| JP | 2004-237144 A | 8/2004 |
| JP | 2004-298139 | 10/2004 |
| JP | 2005-152763 A | 6/2005 |

\* cited by examiner

*Primary Examiner* — William H Beisner
(74) *Attorney, Agent, or Firm* — Nixon & Vanderhye P.C.

(57) ABSTRACT

In a bioreactor, a culture solution derived from a cultivation tank is separated into bacteria cells and filtrate by a bacteria cell filter. The filtrate is introduced from the bacteria cell filter into a micro-nano bubble generation tank where micro-nano-bubbles are mixed with the filtrate. The filtrate containing micro-nano-bubbles is returned to the cultivation tank to activate the microorganisms therein, so that a biological reaction time is reduced by the activated microorganisms.

10 Claims, 7 Drawing Sheets

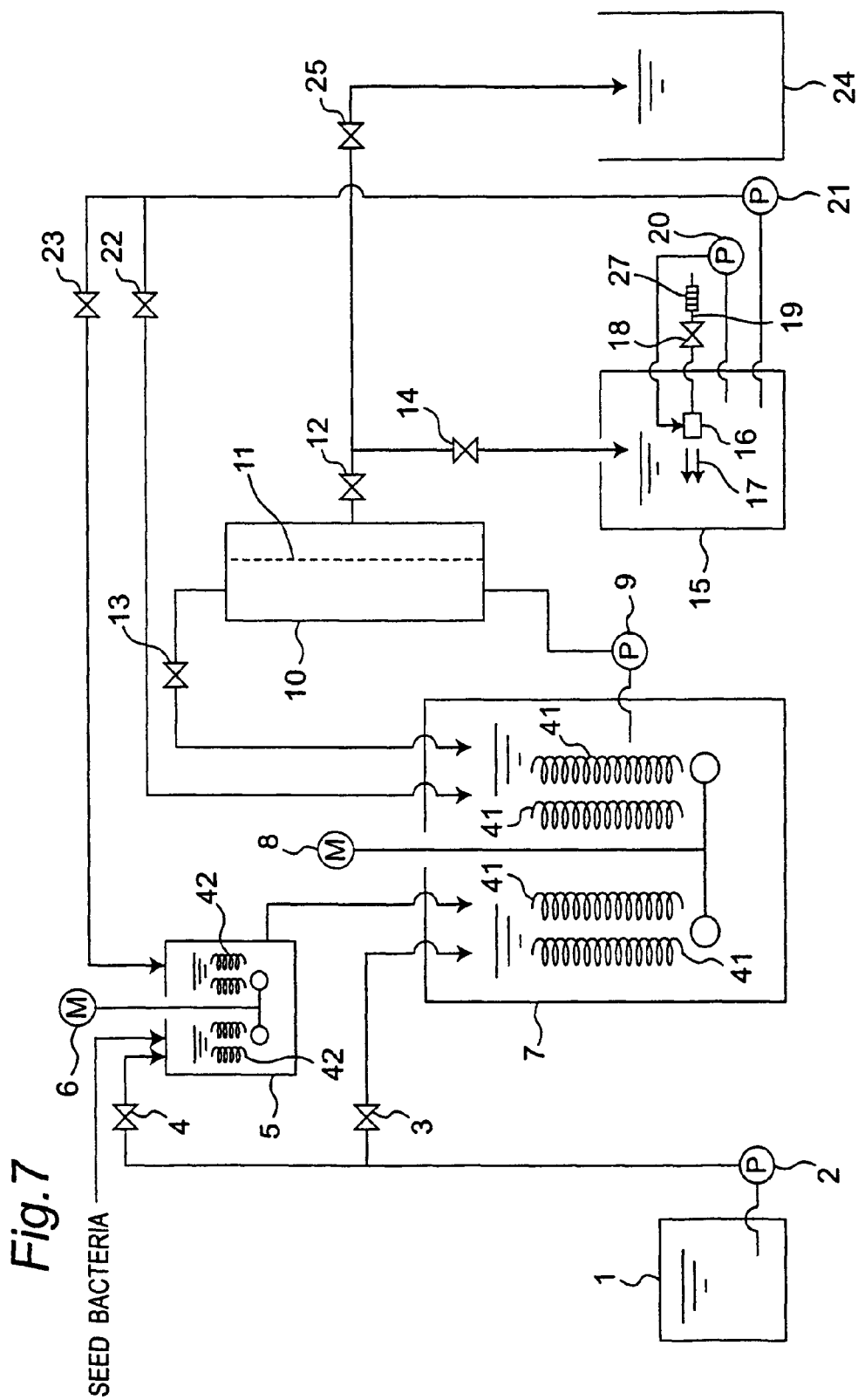

BIOLOGICAL REACTION METHOD AND BIOREACTOR

CROSS-REFERENCE TO RELATED APPLICATION

This nonprovisional application claims priority under 35 U.S.C. §119(a) on Patent Application No. 2006-146247 filed in Japan on 26 May 2006, the entire contents of which are incorporated herein by reference.

BACKGROUND OF THE INVENTION

The present invention relates to a biological reaction method and a bioreactor, specifically to a biological reaction method and a bioreactor in which micro-nano-bubbles are generated to activate microorganisms in a biological reaction so as to efficiently promote the biological reaction by the activated microorganisms.

Although the biological reaction itself is slow unlike the chemical reaction, the biological reaction is gentle and significant for natural environment since it needs to use neither large energy nor many chemical substances.

However, the reaction takes long time since the speed of gentle biological reaction is slow. Therefore, in modern days, there have been many cases where the biological reaction has been not adopted due to the above-stated aspect of time.

The biological reaction has so far given a number of satisfactory results with respect to (i) start of industrial production of amylase, (ii) start of industrial production of isomerized sugar, (iii) development of the manufacturing method for L-ricin, (iv) development of the manufacturing method for D-amino acid, and the like.

As stated above, the biological reaction generally tends to be gentle and therefore slow, and also tends to be unstable in quality. Specifically, the biological reactions take several hours to several days or, in the case of taking particularly long time, require reaction time of several weeks or more. On the other hand, many chemical reactions provide sufficient results in less than one hour.

Accordingly, there are demands for reduction in the biological reaction time and reinforcement of the effects in the biological reaction. If the biological reaction comes to be adopted in many processes, these processes using the biological reaction become beneficial in view of the environmental aspect. However, the biological reaction has been such a problem that offers fewer merits than the chemical reaction in reality.

BRIEF SUMMARY OF THE INVENTION

An object of the present invention is to provide a biological reaction method and a bioreactor which can reduce biological reaction time and improve quality of biological reactants.

In order to achieve the above-mentioned object, the present invention provides a biological reaction method, comprising the steps for:

adding micro-nano-bubbles into a culture solution; and
cultivating microorganisms in the culture solution containing the micro-nano-bubbles in a biological reaction tank.

According to the invention, the microorganisms are cultivated in the culture solution with use of micro-nano-bubbles being added thereinto. Thereby, the activity of the microorganisms is increased, and the efficiency of the biological reaction is enhanced. Therefore, it becomes possible to reduce in biological reaction time by the microorganisms in the biological reaction tank and improve quality of objects such as microbial metabolites obtained by the biological reaction.

The present invention also provides a bioreactor comprising a biological reaction tank for cultivating microorganisms in a culture solution containing the micro-nano-bubbles.

According to the present invention, the efficiency of the biological reaction in the biological reaction tank can be enhanced by the microorganisms, which have high activities increased by the culture solution containing micro-nano-bubbles. Also, the microorganisms activated by the micro-nano-bubbles make it possible to reduce biological reaction time and to enhance quality of reactants (objects), such as microbial metabolites obtained by the biological reaction.

In one embodiment of the present invention, the bioreactor further comprises a seed bacteria cultivation tank for cultivating microorganisms as seed bacteria in the culture solution containing the micro-nano-bubbles and for introducing the culture solution containing the seed bacteria into the biological reaction tank.

According to the bioreactor of this embodiment, the microorganisms as seed bacteria are drastically activated by the micro-nano-bubbles in the seed bacteria cultivation tank and then introduced into the biological reaction tank (cultivation tank). This makes it possible to reduce the biological reaction time and to improve quality of reactants by the biological reaction in the seed bacteria cultivation tank and the biological reaction tank.

In one embodiment of the present invention, the bioreactor further comprises:

a medium reservoir for supplying a medium to the biological reaction tank;
a bacteria cell filter for receiving the culture solution from the biological reaction tank and separating the culture solution into bacteria cells and filtrate; and
a micro-nano bubble generation tank for receiving the filtrate from the bacteria cell filter, adding the micro-nano-bubbles to the filtrate, and introducing the filtrate containing the micro-nano-bubbles into at least one of the seed bacteria cultivation tank and the biological reaction tank.

According to the bioreactor of this embodiment, the bacteria cell filter separates the culture solution, which is derived from the biological reaction tank, into bacteria cells and filtrate. Then, the filtrate from the bacteria cell filter is introduced into the micro-nano bubble generation tank. Therefore, the generation state of the micro-nano-bubbles can be checked at this micro-nano bubble generation tank. Since the generation state of the micro-nano-bubbles can be checked, the air quantity of the micro-nano bubble generator can be adjusted into an optimal condition.

In one embodiment of the present invention, the bioreactor further comprises an air supply section for supplying air disinfected with a disinfection filter to the seed bacteria cultivation tank and the biological reaction tank, and for aerating and stirring the seed bacteria cultivation tank and the biological reaction tank.

According to this embodiment, the air supply section supplies air, which is disinfected with the disinfection filter, to the seed bacteria cultivation tank and the biological reaction tank for aeration and stir. Therefore, aerobic microorganisms can be cultivated without the influence of other various germs in the seed bacteria cultivation tank and the biological reaction tank.

In one embodiment of the present invention, the bioreactor further comprises:

a medium adjustment tank for adjusting a plurality of raw media materials; and a sterilization section for sterilizing the raw media materials adjusted in the medium adjustment tank and introducing the sterilized raw media materials into the medium reservoir.

According to this embodiment, the plurality of raw media materials are adjusted in the medium adjustment tank and sterilized in the sterilizing section before being introduced into the medium reservoir. Therefore, the adjusted raw media materials are introduced into the medium reservoir without being influenced by other various germs.

In one embodiment of the present invention, the bioreactor further comprises:

a filtrate reservoir for receiving the filtrate from the bacteria cell filter and adding the micro-nano-bubbles to the filtrate; and a distiller for receiving the filtrate containing the micro-nano-bubbles from the filtrate reservoir and distilling the filtrate containing the micro-nano-bubbles.

According to this embodiment, the filtrate before being distilled with the distiller contains micro-nano-bubbles in addition to moisture and target metabolites (such as ethanol). Therefore, distillation can be conducted at a lower temperature than that in the case where the distiller does not contain micro-nano-bubbles. This allows energy saving and improvement in quality of target metabolites under the better conditions for distillation.

In one embodiment of the present invention, the filtrate reservoir has a micro-nano bubble generator.

According to this embodiment, the micro-nano bubble generator for generating micro-nano-bubbles is placed in the filtrate reservoir, so that the micro-nano-bubbles can efficiently be added into the filtrate in the filtrate reservoir.

In one embodiment of the present invention, a filler material is placed in the biological reaction tank.

According to this embodiment, the biological reaction tank, which is a cultivation tank, is filled with a filler material. Therefore, microorganisms can be propagated on the filler material, so that smooth and stable cultivation is achieved.

In one embodiment of the present invention, the filler material is a string-type polyvinylidene chloride filler.

According to this embodiment, the string-type polyvinylidene chloride filler is a filler material which not only allows easy procurement at a low cost as a filler material but also has a considerably large surface area. Therefore, a large amount of microorganisms can be cultivated in a stable manner.

In one embodiment of the present invention, a filler material is placed in the seed bacteria cultivation tank.

According to this embodiment, the seed bacteria can stably be immobilized and cultivated on the filler material which is placed in the seed bacteria cultivation tank.

In one embodiment of the present invention, the filler material is a string-type polyvinylidene chloride filler.

According to this embodiment, the string-type polyvinylidene chloride filler is durable, which filler is placed in the seed bacteria cultivation tank. Therefore, the filler withstands a prolonged use and is long lasting. Further, the filler is negatively charged, so that immobilization of microorganisms is easy to achieve.

In one embodiment of the present invention, the biological reaction tank and the seed bacteria cultivation tank are filled with a filler material.

According to this embodiment, microorganisms can be immobilized on the filler material which fills the biological reaction tank (cultivation tank) and the seed bacteria cultivation tank, and thereby high density cultivation becomes possible. This makes it possible to reduce cultivation time and improve quality of reactants obtained by the biological reaction.

In the bioreactor in one embodiment, the filler material is a string-type polyvinylidene chloride filler.

According to the bioreactor of this embodiment, the string-type polyvinylidene chloride filler is durable, withstands prolonged use and is long lasting. Further, the string-type polyvinylidene chloride filler is negatively charged, so that microorganisms are easily immobilized. Moreover, the microorganisms can be cultivated at high concentration on the string-type polyvinylidene chloride filler. This makes it possible to reduce cultivation time and improve quality of biological reactants.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 7 is a schematic view showing a bioreactor in a seventh embodiment of the present invention.

DETAILED DESCRIPTION OF THE INVENTION

Hereinbelow, the present invention will be described in details in conjunction with the embodiments with reference to the drawings.

First Embodiment

Figure 1:
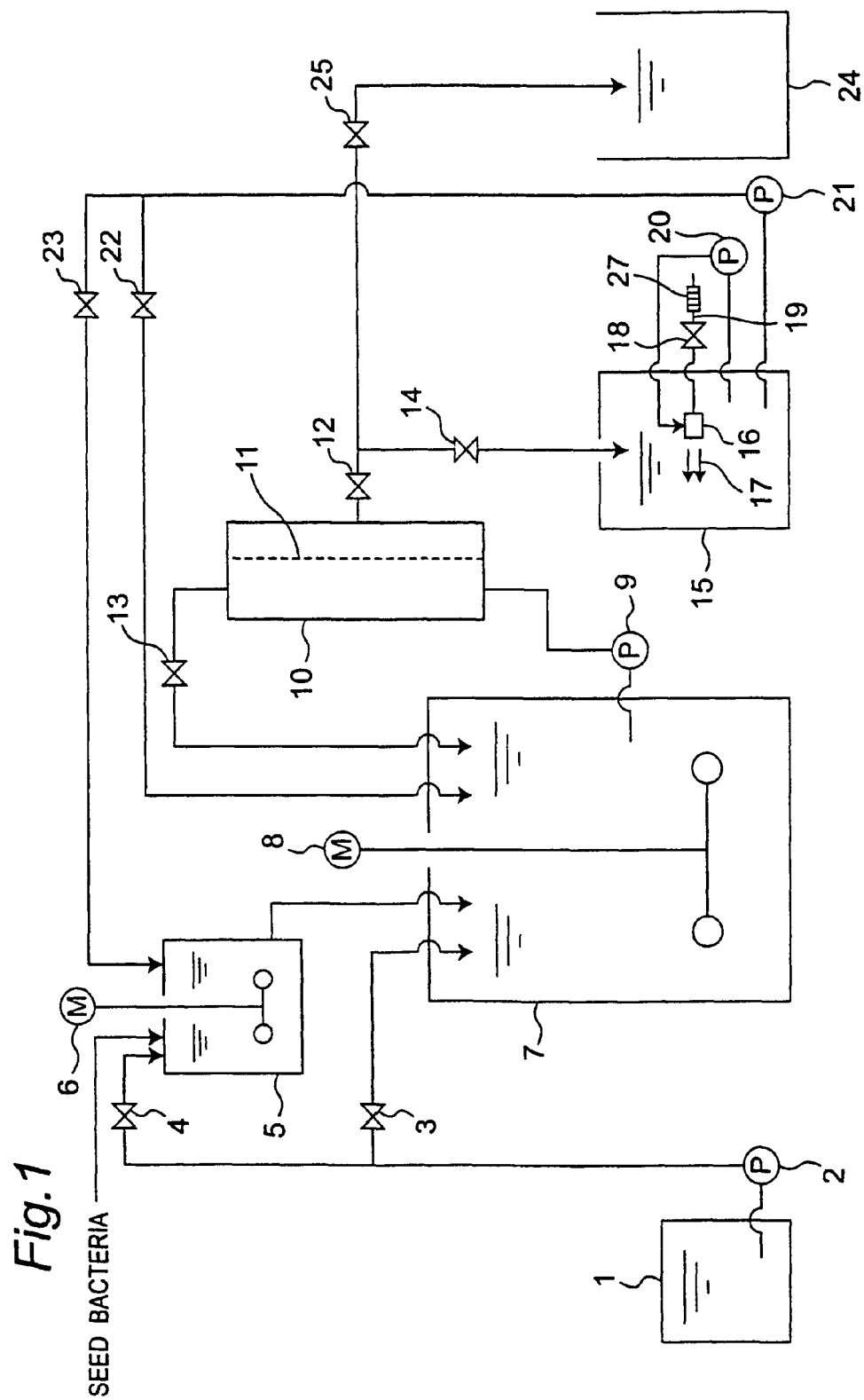
FIG. 1 is a schematic view showing a bioreactor in a first embodiment of the present invention.

FIG. 1 is a schematic view showing a bioreactor in a first embodiment of the present invention. This first embodiment is composed of a medium reservoir 1, a seed bacteria cultivation tank 5, a cultivation tank 7 as a biological reaction tank, a bacteria cell filter 10, a micro-nano bubble generation tank 15, and a filtrate reservoir 24.

In FIG. 1, a nitrogen source, a carbon source, minerals, vitamins and the like are fed to and mixed in the medium reservoir 1. The liquid medium in the medium reservoir 1 is transported to the seed bacteria cultivation tank 5 by a medium reservoir pump 2 when a valve 4 is opened and a valve 3 is closed.

When cultivation with seed bacteria is completed in the cultivation tank 7 with a result that cultivation of microorganisms is stable, then the valve 3 is put in the opened state while the valve 4 is put in the closed state. The liquid medium is directly transported from the medium reservoir 1 to the cultivation tank 7 by the medium reservoir pump 2. However, in this way the liquid medium is directly transported from the medium reservoir 1 to the cultivation tank 7 only when a sufficient time has elapsed after a trial run in the cultivation tank 7.

Anyway, at first, the liquid medium from the medium reservoir 1 is introduced into the seed bacteria cultivation tank 5, where seed bacteria and liquid medium is stirred by a stirrer 6, so as to cultivate the seed bacteria.

The purpose of the seed bacteria cultivation tank 5 is to cultivate bacteria of an initial mass required to cultivate microorganisms in the cultivation tank 7 which is a main cultivation tank.

The target microbial metabolites are acquired basically from the cultivation tank 7. Specifically, in this embodiment, the cultivation in the seed bacteria cultivation tank 5 constitutes a biological reaction in the first stage, and the subsequent microbial cultivation in the cultivation tank 7 constitutes a biological reaction in the second stage.

More specifically, when sufficient seed bacteria have been cultivated in the seed bacteria cultivation tank 5, a culture solution for seed bacteria is introduced from the seed bacteria cultivation tank 5 into the cultivation tank 7 by gravity flow. Then, the valve 3 is open while the valve 4 is closed, so that the liquid medium is supplied from the medium reservoir 1 to the cultivation tank 7 by the medium reservoir pump 2.

The cultivation tank 7 is equipped with a cultivation tank stirrer 8 for stirring the content of the tank. The liquid medium, which is introduced from the medium reservoir 1 into the cultivation tank 7 in the state that the valve 3 is opened and the valve 4 is closed, is stirred by the cultivation tank stirrer 8 so that microorganisms are cultivated. The cultivation tank 7 is also equipped with a device (unshown) which controls temperature and pH of the culture solution for cultivating microorganisms.

In this embodiment, a micro-nano bubble generation tank 15 is placed on the downstream side of the bacteria cell filter 10 so as to shorten the cultivation time in the cultivation tank 7 as compared with the conventional example.

Specifically, in a first case, during cultivation in the cultivation tank 7, the valves 12 and 14 are opened while the valves 13 and 25 are closed. Thereby, the culture solution is introduced from the cultivation tank 7 into the bacteria cell filter 10 by using the cultivation tank pump 9, so that the culture solution is filtered in the bacteria cell filter 10 so as to obtain the filtrate. Then, the filtrate is introduced into the micro-nano bubble generation tank 15. Micro-nano-bubbles are generated in the micro-nano bubble generation tank 15 so as to mix the micro-nano-bubbles into the filtrate. Also, when the valve 22 is opened and the valve 23 is closed, the filtrate containing micro-nano-bubbles is returned to the cultivation tank 7. Thereby, the microorganisms in the cultivation tank 7 are activated by the micro-nano-bubbles, so that it becomes possible to reduce the biological reaction time.

In a second case, during cultivation in the cultivation tank 7, the valves 12 and 14 are also opened while the valves 13 and 25 are also closed. At the same time, depending on the water quality of the culture solution in the cultivation tank 7, the valve 23 is opened while the valve 22 is closed. Thereby, new seed bacteria in the seed bacteria cultivation tank 5 are mixed with the filtrate containing micro-nano-bubbles, so that the new seed bacteria can be more activated in cultivation. Then, microorganisms, which are activated as seed bacteria in the seed bacteria cultivation tank 5, can be introduced by gravity flow to the cultivation tank 7 and be cultivated therein.

The choice between the first case and the second case should be determined on the basis of the production condition of the target microbial metabolites.

In this way, the filtrate containing micro-nano-bubbles is introduced into the cultivation tank 7 and the seed bacteria cultivation tank 5, so that microorganisms propagating in the cultivation tank 7 and the seed bacteria cultivation tank 5 can be activated further. As the result, the reaction time can be reduced.

When cultivation is completed in the cultivation tank 7 after a predetermined time, the cultivation tank pump 9 is operated, so that the culture solution is passed through the bacteria cell filter 10 and separated into bacteria cells and filtrate. The cell filter 10 is equipped with a membrane filter 11. The membrane filter 11 is a porous film having a pore size which is large enough to pass the culture solution but small enough to block microorganisms. A ceramic filter element or a synthetic polymer film, which can be sterilized, is employed for the membrane filter 11.

Microbial metabolites namely filtrate, as a product, can be stored in the filtrate reservoir 24 in the case where the valves 13 and 14 are closed while the valves 12 and 25 are opened at the time of operating the cultivation tank pump 9.

The bioreactor of this embodiment is applicable to the field of foodstuffs, medicines and the like where the biological reaction such as brewing or fermentation is used. As stated above, microorganisms are activated by using micro-nano-bubbles, which makes it possible to reduce a biological reaction time and improve quality of biological reactants.

More specifically, microorganisms in solution are cultivated in the cultivation tank 7, and thereafter, the solution is separated for refining into bacteria cells (microorganisms) and fluid (filtrate) in the bacteria cell filter 10. After the bacteria cell separation, micro-nano-bubbles are added to the fluid (filtrate), and then, the fluid containing the micro-nano-bubbles is returned to the seed bacteria cultivation tank 5 and to the cultivation tank 7 which are located upstream from the micro-nano bubble generation tank 15. Thereby, microorganisms are activated, so that the reaction time can be reduced in cultivation tank 7.

The bioreactor of this embodiment can be used not only in the field of wastewater treatment, but also widely in other industrial fields such as the food stuff industry or the pharmaceutical industry.

In this embodiment, micro-nano-bubbles are generated in the filtrate from the bacteria cell filter 10, so that it is possible to suppress clogging in the micro-nano bubble generator 16. In contrast, the micro-nano bubble generator tends to suffer clogging due to the existence of the bacteria in the case where micro-nano-bubbles are generated in the liquid containing bacteria cells, specifically, in the cultivation tank 7 and the seed bacteria cultivation tank 5. In short, the present embodiment has an advantage of less clogging since micro-nano bubble generation is performed in the filtrate which contains little bacteria cells.

The seed bacteria cultivation tank 5 needs to be operated in the early operation stages of the cultivation tank 7 where essential fermentation and the like are performed. However, it becomes unnecessary to operate the seed bacteria cultivation tank 5 in the operational state achieved in a predetermined time after the cultivation tank 7 is set in motion. In the seed bacteria cultivation tank 5, where culture media (foods for microorganisms) have been supplied, early cultivation of microorganisms is performed with use of seed bacteria. The standard cultivation amount of the seed bacteria cultivation tank 5 is about 1 ton for example. In this case, the cultivation amount of the cultivation tank 7 is about 10 tons.

The micro-nano bubble generator 16 is placed inside the micro-nano bubble generation tank 15. Also, equipment relating to this micro-nano bubble generator 16 is placed therein.

In the micro-nano bubble generation tank 15, a water stream 17 is generated by the fine bubbles which are discharged from the micro-nano bubble generator 16. The water stream 17 turns into a circulating water stream in the micro-nano bubble generation tank 15, and stirs the content of the tank. In other words, the micro-nano bubble generator 16 generates a micro-nano-bubble stream so as to mix filtrate with micro-nano-bubbles. The required amount of the circulating water is supplied to the micro-nano bubble generator 16 by means of a circulating pump 20. The required amount of disinfected air, which passes through the disinfection filter 27 and an air suction pipe 19, is adjusted by a valve 18 before being supplied to the micro-nano bubble generator 16. This makes it possible to generate optimal micro-nano-bubbles in micro-nano bubble generator 16.

Here, the micro-bubbles are defined as bubbles having the diameter size of 10 to several dozen μm. The nano-bubbles are defined as bubbles having the diameter size of several 100 nm or less. The micro-nano-bubbles include the micro-bubbles and the nano-bubbles, so that the micro-nano-bubbles have the size of about 100 nm to 10 μm ($10^4$ nm). The micro-bubbles change to micro-nano-bubbles due to contraction movements after their generation.

Second Embodiment

Figure 2:
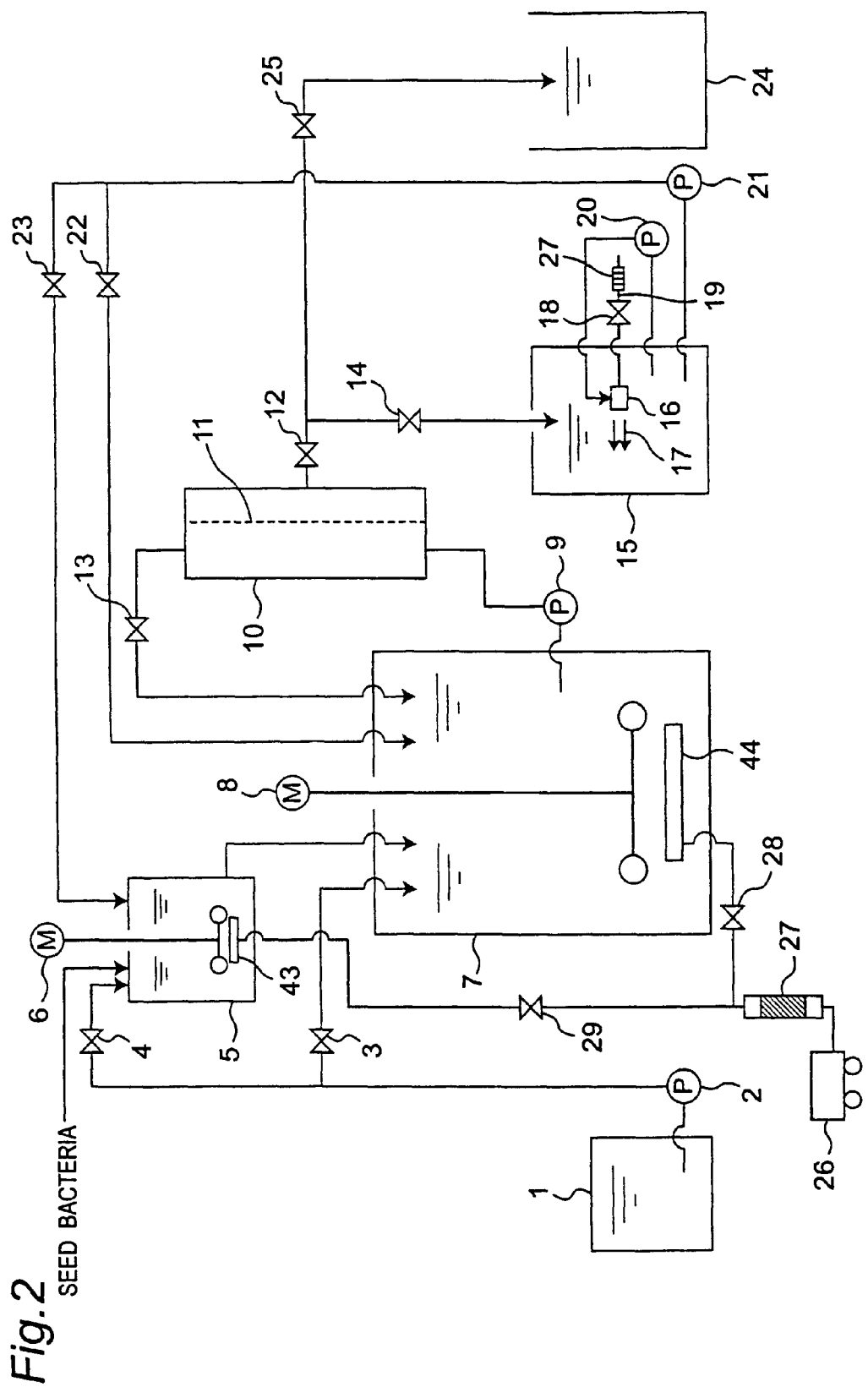
FIG. 2 is a schematic view showing a bioreactor in a second embodiment of the present invention.

Next, FIG. 2 is a schematic view showing a bioreactor in a second embodiment of the present invention. The second embodiment is different from the first embodiment shown in FIG. 1 in the points that an air diffusing pipe 43 is placed in the seed bacteria cultivation tank 5, that an air diffusing pipe 44 is placed in the cultivation tank 7, and that a compressor 26, as an air supply section, is connected to the air diffusing pipes 43 and 44 via the disinfection filter 27. In the second embodiment, therefore, component members identical to those in the first embodiment are designated by identical reference numerals, and description will be given of only the portions different from the first embodiment.

In the second embodiment, the air discharged from the compressor 26 is disinfected by the disinfection filter 27. Thereafter, the air is used for air discharged into the seed bacteria cultivation tank 5 from the air diffusing pipe 43 and air discharged to the cultivation tank 7 from the air diffusing pipe 44. Therefore, the disinfected air aerates and stirs the contents in the seed bacteria cultivation tank 5 and the cultivation tank 7, so that aerobic microorganisms can be propagated in the seed bacteria cultivation tank 5 and the cultivation tank 7 without influence of other various germs. Therefore, the second embodiment is suitable in the case where the target microbial metabolites are metabolic products of aerobic microorganisms.

In the second embodiment, micro-nano-bubbles is added to and mixed with the filtrate, which is derived from the bacteria cell filter 10, in the micro-nano bubble generation tank 15. The filtrate having micro-nano-bubbles is introduced into the seed bacteria cultivation tank 5 and the cultivation tank 7 by using a return pump 21. Thereby, it becomes possible to achieve significant improvement in production quantity of the metabolic products.

The valve 28 quantitatively adjusts or stops the air discharged to the cultivation tank 7 from the air diffusing pipe 44. Also, the valve 29 quantitatively adjusts or stops the air discharged to the seed bacteria cultivation tank 5 from the air diffusing pipe 43.

Third Embodiment

Figure 3:
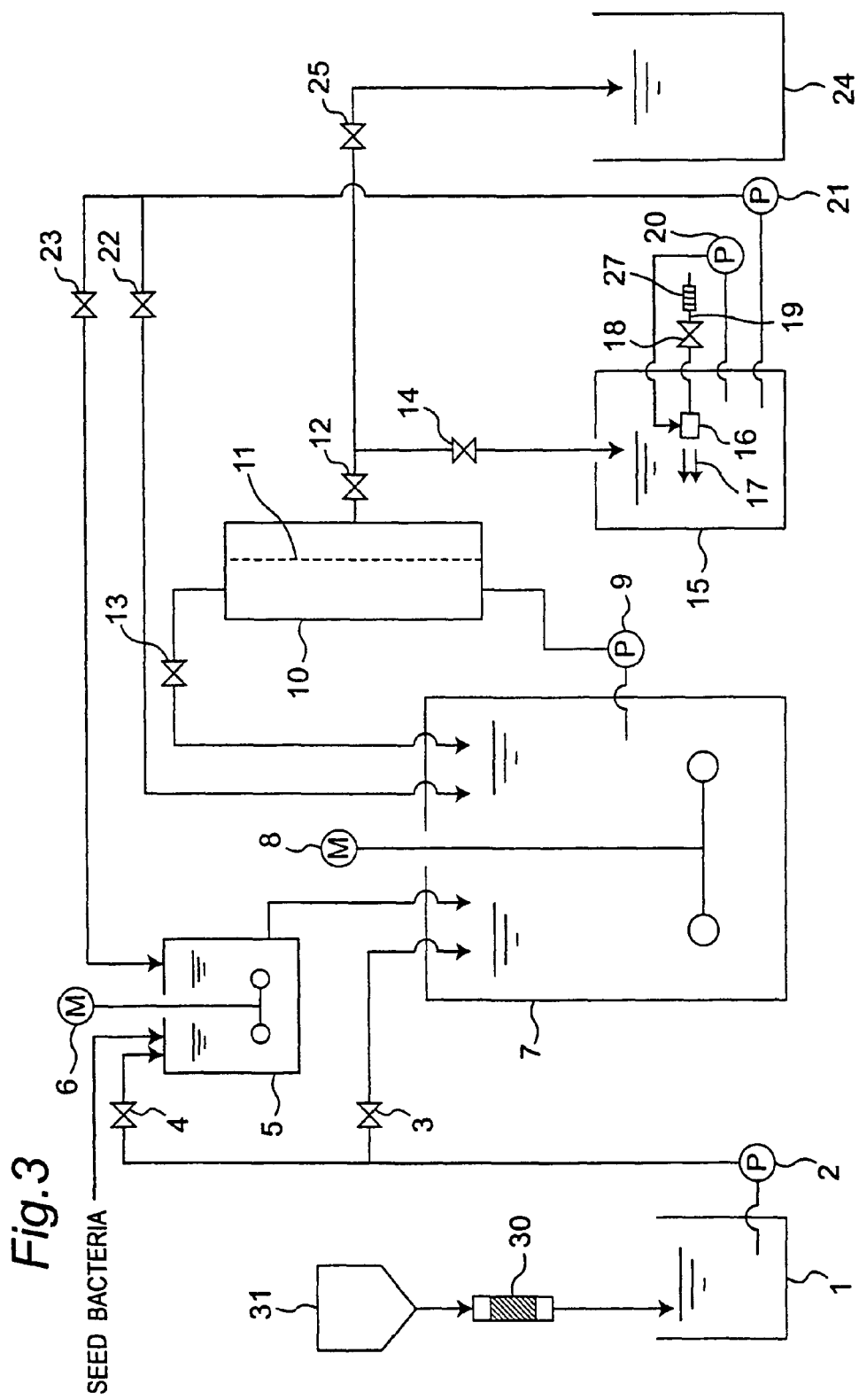
FIG. 3 is a schematic view showing a bioreactor in a third embodiment of the present invention.

Next, FIG. 3 is a schematic view showing a bioreactor in a third embodiment of the present invention. The third embodiment is different from the first embodiment shown in FIG. 1 in the point that a medium adjustment tank 31 and a sterilization section 30 below the medium adjustment tank 31 are placed above the medium reservoir 1. Therefore, in the third embodiment, component members identical to those in the first embodiment are designated by identical reference numerals, and description will mainly be given of only the portions different from the first embodiment.

In the third embodiment, two or more kinds of raw media materials are mixed and adjusted in the medium adjustment tank 31. The two or more kinds of materials mixed in the medium adjustment tank 31 are sterilized in the sterilizing section 30, and thereafter introduced into the medium reservoir 1 by gravity flow.

In the third embodiment, the mixed materials are sterilized, and therefore, without generating any contamination caused by various germs, it is possible to introduced into the cultivation tank 7 the raw media materials obtained by mixing various kinds of materials. Thus, microbial cultivation is certainly performed in the cultivation tank 7 with use of the raw media materials satisfying the cultivation conditions of the target microorganisms.

Fourth Embodiment

Figure 4:
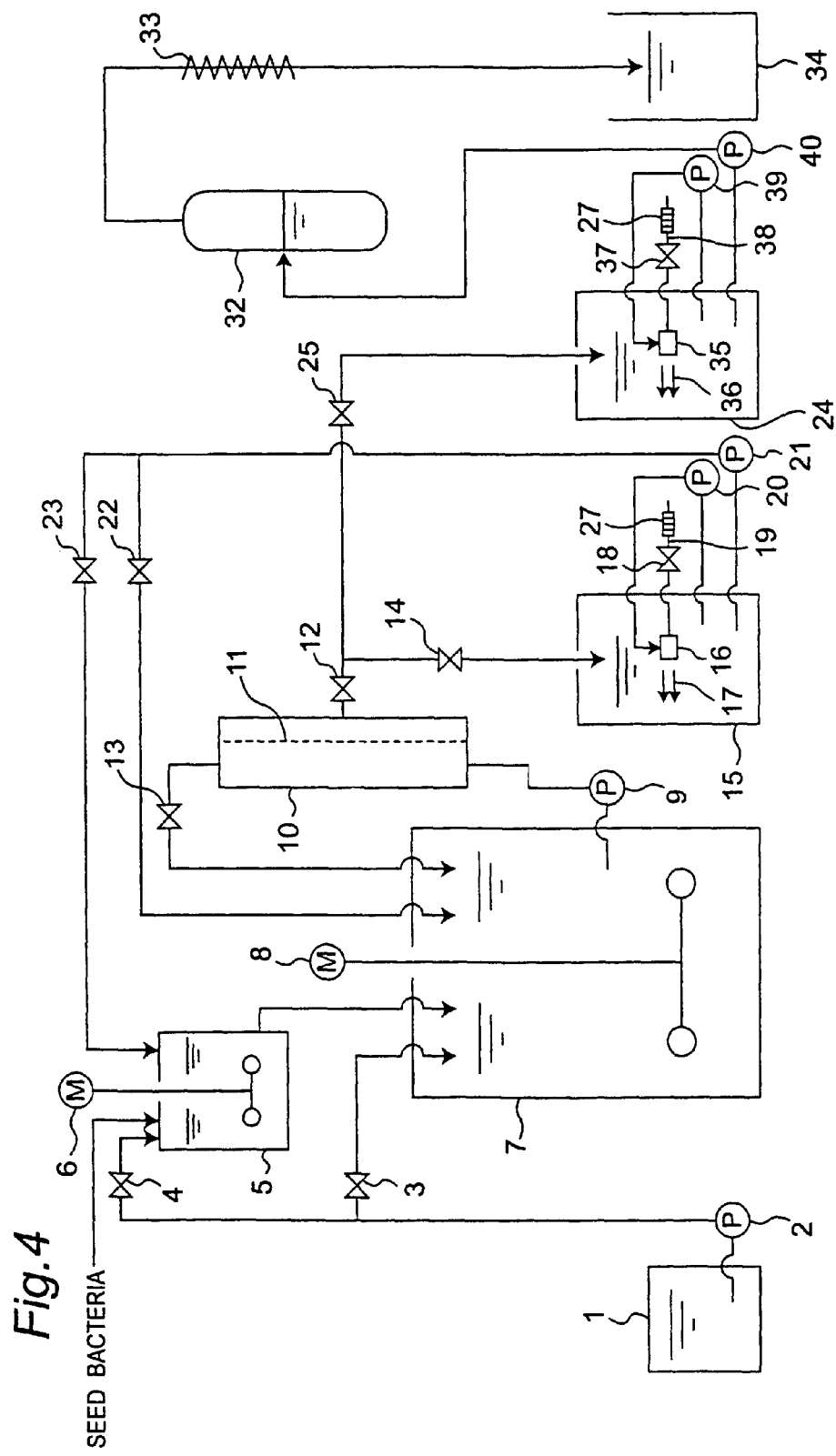
FIG. 4 is a schematic view showing a bioreactor in a fourth embodiment of the present invention.

FIG. 4 is a schematic view showing a bioreactor in a fourth embodiment of the present invention. The fourth embodiment is different from the first embodiment in the points that a micro-nano bubble generator 35 is placed in the filtrate reservoir 24 of the first embodiment shown in FIG. 1, and that there are provided a distiller 32 for receiving filtrate containing micro-nano-bubbles from this filtrate reservoir 24, a cooling condenser 33 and a condensed liquid tank 34 located downstream from the distiller 32. Therefore, in the fourth embodiment, component members identical to those in the first embodiment are designated by identical reference numerals, and description will be given of only the portions different from the first embodiment.

In the fourth embodiment, a micro-nano bubble generator 35 is placed in the filtrate reservoir 24, so that the filtrate contains micro-nano-bubbles in the filtrate reservoir 24. The filtrate containing micro-nano-bubbles from this filtrate reservoir 24 are supplied via the distiller 32 to the cooling condenser 33 for condensing into a target product therein. The target product is collected in the condensed liquid tank 34.

A water stream 36 is generated in the filtrate reservoir 24 by fine bubbles discharged from the micro-nano bubble generator 35. The water stream 36 is in the form of a circulating water stream, and stirs the contents in the filtrate reservoir 24. The micro-nano bubble generator 35 generates a micro-nano-bubble stream so as to mix filtrate with micro-nano-bubbles.

The filtrate reservoir 24 is equipped with equipment relating to the micro-nano bubble generator 35. Specifically, a circulating pump 39 supplies a required amount of circulating water to the micro-nano bubble generator 35. A disinfection filter 27 disinfects the air, and a valve 37 quantitatively adjusts the disinfected air passed through air suction pipe 38, thereby the required amount of disinfected air is supplied to the micro-nano bubble generator 35. Thus, the micro-nano bubble generator 35 generates optimal micro-nano-bubbles.

In the fourth embodiment, the filtrate containing micro-nano-bubbles is introduced into the distiller 32 from filtrate reservoir 24 by using a filtrate reservoir pump 40. Thus, distillation is easily achieved in the distiller 32, and condensation is easily achieved in the cooling condenser 33. In the case of alcoholic fermentation for example, specifically, in the case of increasing the alcohol concentration in liquor after the alcoholic fermentation, it is possible to distill and refine the liquor at a lower temperature if the fermentation liquor containing micro-nano-bubbles is distilled. This is because micro-nano-bubbles exist in the liquor. This allows considerable energy saving and improvement in quality of target metabolites since distillation conditions change for the better.

Fifth Embodiment

Figure 5:
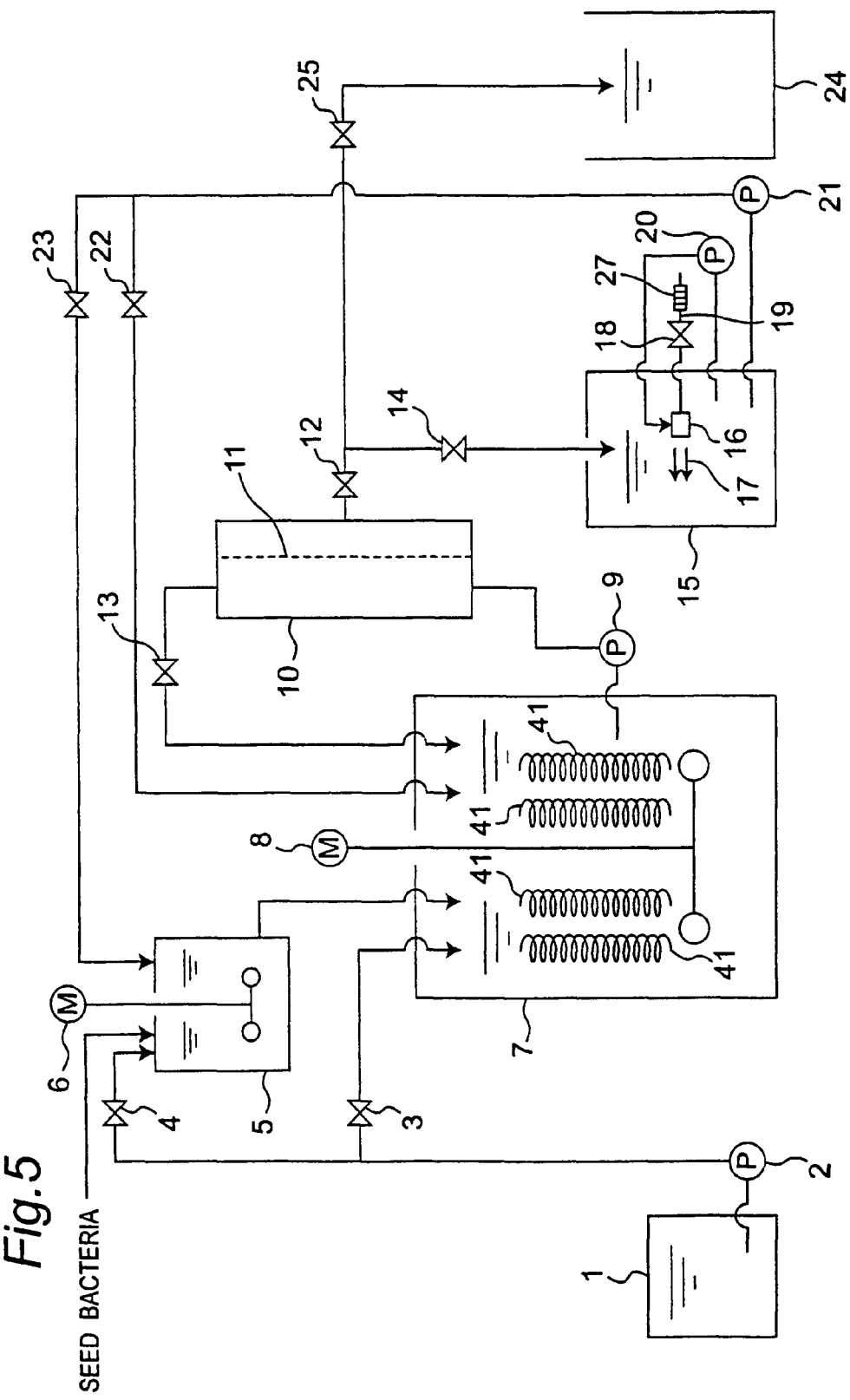
FIG. 5 is a schematic view showing a bioreactor in a fifth embodiment of the present invention.

Next, FIG. 5 is a schematic view showing a bioreactor in a fifth embodiment of the present invention. A bioreactor of the fifth embodiment is different from the first embodiment in the point that a string-type polyvinylidene chloride filler 41, as a filler material, is placed in the cultivation tank 7 in the first embodiment shown in FIG. 1. Therefore, in the fifth embodiment, component members identical to those in the first embodiment are designated by identical reference numerals, and description will be given of only the portions different from the first embodiment.

The string-type polyvinylidene chloride filler 41 according to the fifth embodiment, which is placed in the cultivation tank 7, is not only easily procured at a low cost, but also has a considerably large surface area. Further, the string-type polyvinylidene chloride filler 41 is durable so that it withstands a prolonged use and has a longer operating life. Furthermore, the string-type polyvinylidene chloride filler 41 is negatively-charged, so that microorganisms are easily immobilized. Thus, the string-type polyvinylidene chloride filler 41 allows microorganisms activated by micro-nano-bubbles to be cultivated in large amounts at a high concentration. This is consequently expected to reduce reaction time in the cultivation tank 7 and improve quality of the culture solution.

Sixth Embodiment

Figure 6:
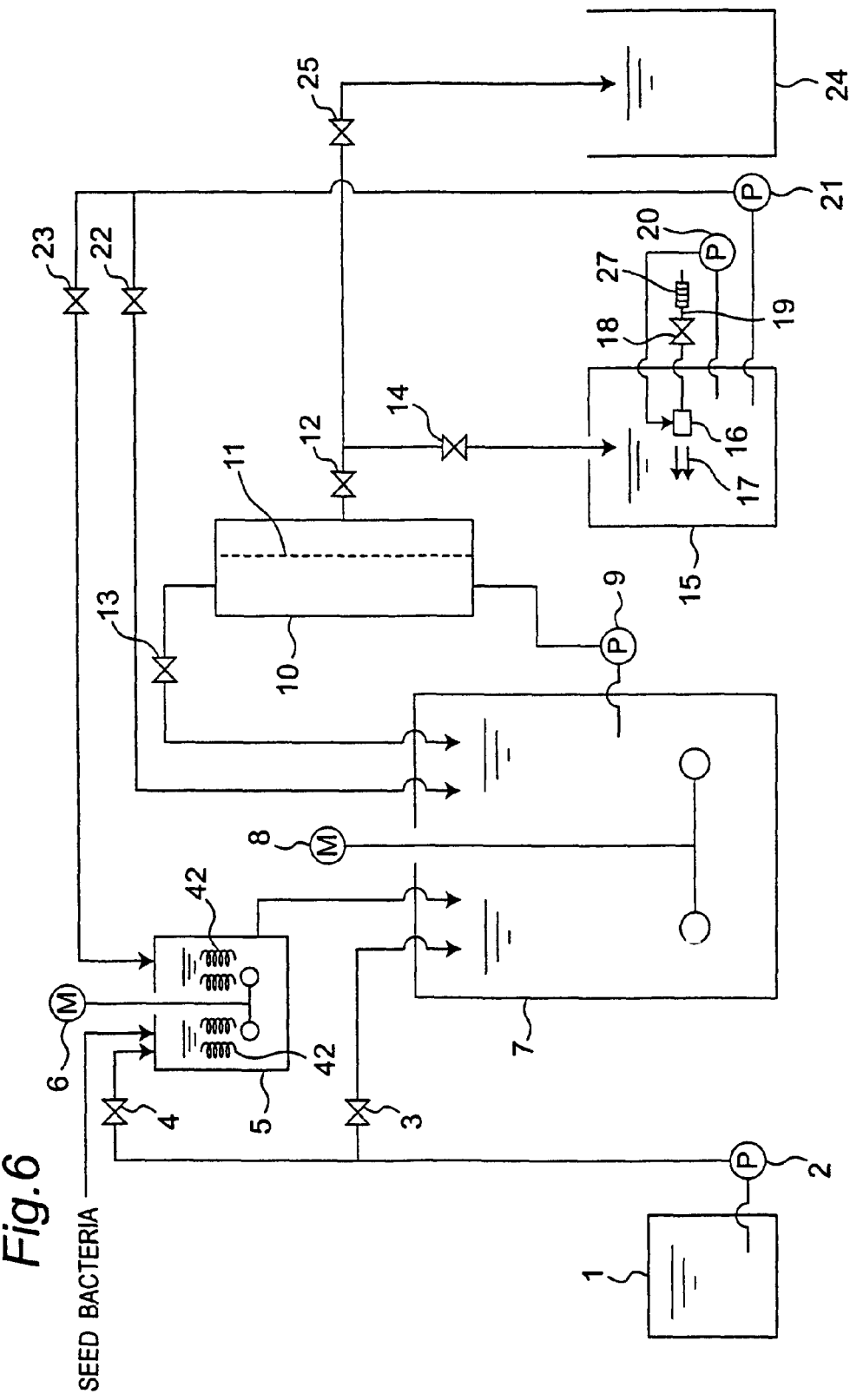
FIG. 6 is a schematic view showing a bioreactor in a sixth embodiment of the present invention.

Next, FIG. 6 is a schematic view showing a bioreactor in a sixth embodiment of the present invention. The sixth embodiment is different from the first embodiment in the point that a string-type polyvinylidene chloride filler 42 is placed in the seed bacteria cultivation tank 5 in the first embodiment shown in FIG. 1. Therefore, in the sixth embodiment, component members identical to those in the first embodiment are designated by identical reference numerals, and description will mainly be given of only the portions different from the first embodiment.

In the sixth embodiment, the seed bacteria cultivation tank 5 is filled with the string-type polyvinylidene chloride filler 42, so that microorganisms activated by micro-nano-bubbles can be cultivated in large amounts on the string-type polyvinylidene chloride filler 42. Consequently, it becomes possible to reduce the reaction time in the seed bacteria cultivation tank 5 and to improve the quality of the culture solution therein. By introducing microorganisms activated in the seed bacteria cultivation tank 5 into the cultivation tank 7, it becomes possible to reduce the reaction time in the cultivation tank 7 and enhance the quality of the culture solution therein.

Seventh Embodiment

Next, FIG. 7 is a schematic view showing a bioreactor in a seventh embodiment of the present invention. The seventh embodiment is different from the first embodiment in the point that a string-type polyvinylidene chloride filler 42 is placed in the seed bacteria cultivation tank 5 and a string-type polyvinylidene chloride filler 41 is placed in the cultivation tank 7, where the seed bacteria cultivation tank 5 and the cultivation tank 7 are those in the first embodiment shown in FIG. 1. Therefore, in the seventh embodiment, component members identical to those in the first embodiment are designated by identical reference numerals, and description will mainly be given of only the portions different from the first embodiment.

In the seventh embodiment, microorganisms activated by micro-nano-bubbles are cultivated in large amounts on the string-type polyvinylidene chloride filler 42 placed in the seed bacteria cultivation tank 5 and the string-type polyvinylidene chloride filler 42 placed in the cultivation tank 7, respectively. Consequently, it becomes possible to reduce the reaction times in the seed bacteria cultivation tank 5 and the cultivation tank 7, and to improve the quality of the culture solution.

It is to be noted that the string-type polyvinylidene chloride fillers 41 and 42 in the fifth to seventh embodiments may be replaced with polyvinylidene chloride fillers having other shapes. Further, it is acceptable to employ fillers made of other materials and having other shapes than the above.

EXPERIMENTAL EXAMPLE

An experimental device for ethanol production was manufactured as a bioreactor corresponding to the first embodiment shown in FIG. 1. The capacity of the medium reservoir 1 in this experimental device was about $0.5 \, m^3$, the capacity of the seed bacteria cultivation tank 5 was about $1 \, m^3$, and the capacity of the cultivation tank 7 was about $3 \, m^3$. The capacity of the bacteria cell filter 10 was about $0.5 \, m^3$, the capacity of the micro-nano bubble generation tank 15 was about $1 \, m^3$, and the capacity of the filtrate reservoir 24 was $0.5 \, m^3$.

The liquid medium, which consists of amino acid, vitamins, inorganic salts and so on, was introduced into the experimental device for ethanol production for the purpose of trial run and cultivation for about one month. After the trial run, an analysis was performed in the filtrate reservoir 24. The analysis result indicated that main ethanol could efficiently be manufactured together with lactic acid, acetic acid and the like.

The invention being thus described, it will be obvious that the invention may be varied in many ways. Such variations are not be regarded as a departure from the spirit and scope of the invention, and all such modifications as would be obvious to one skilled in the art are intended to be included within the scope of the following claims.

The invention claimed is:

1. A bioreactor comprising:
   a medium reservoir for storing a culture solution for microorganisms as seed bacteria;
   a seed bacteria cultivation tank for cultivating the microorganisms to be put in with a mixture of the culture solution supplied from the medium reservoir and micro-nano-bubbles;
   a biological reaction tank for cultivating the microorganisms with solution supplied from the seed bacteria cultivation tank;
   a bacteria cell filter for receiving the culture solution from the biological reaction tank and separating the culture solution into bacteria cells and filtrate;
   a first micro-nano bubble generation tank for receiving the filtrate from the bacteria cell filter and having a micro-nano bubble generator, adding the micro-nano-bubbles to the filtrate by the micro-nano-bubble generator, and introducing the filtrate containing the micro-nano-bubbles into at least the former of the biological reaction tank and the seed bacteria cultivation tank;

a filtrate reservoir being a second micro-nano bubble generation tank for receiving the filtrate from the bacteria cell filter and adding the micro-nano-bubbles to the filtrate; and a distiller for receiving the filtrate containing the micro-nano-bubbles from the filtrate reservoir and distilling the filtrate containing the micro-nano-bubbles.

2. The bioreactor set forth in claim 1, further comprising an air supply section for supplying air disinfected with a disinfection filter to the seed bacteria cultivation tank and the biological reaction tank, and for aerating and stirring the seed bacteria cultivation tank and the biological reaction tank.

3. The bioreactor set forth in claim 1, further comprising:
a medium adjustment tank for adjusting a plurality of raw media materials; and
a sterilization section for sterilizing the raw media materials adjusted in the medium adjustment tank and introducing the sterilized raw media materials into the medium reservoir.

4. The bioreactor set forth in claim 1, wherein the filtrate reservoir has a micro-nano bubble generator.

5. The bioreactor set forth in claim 1, wherein a filler material is placed in the biological reaction tank.

6. The bioreactor set forth in claim 5, wherein the filler material is a string-type polyvinylidene chloride filler.

7. The bioreactor set forth in claim 1, wherein a filler material is placed in the seed bacteria cultivation tank.

8. The bioreactor set forth in claim 7, wherein the filler material is a string-type polyvinylidene chloride filler.

9. The bioreactor set forth in claim 1, wherein the biological reaction tank and the seed bacteria cultivation tank are filled with a filler material.

10. The bioreactor set forth in claim 9, wherein the filler material is a string-type polyvinylidene chloride filler.

* * * * *